United States Patent [19]
Yue et al.

[11] Patent Number: 6,043,056
[45] Date of Patent: Mar. 28, 2000

[54] CELL SURFACE GLYCOPROTEINS

[75] Inventors: Henry Yue, Sunnyvale; Neil C. Corley, Mountain View; Karl J. Guegler, Menlo Park; Gina A. Gorgone, Boulder Creek; Mariah R. Baughn, San Leandro, all of Calif.

[73] Assignee: Incyte Pharmaceuticals, Inc., Palo Alto, Calif.

[21] Appl. No.: 09/187,331

[22] Filed: Nov. 6, 1998

[51] Int. Cl.[7] .............................. C12P 21/06; C12Q 1/68; C12N 1/20; C12N 15/00; C07H 21/02

[52] U.S. Cl. ..................... 435/69.1; 435/6; 435/252.3; 435/320.1; 536/23.1

[58] Field of Search ........................... 435/69.1, 6, 320.1, 435/252.3; 536/23.1

[56] References Cited

PUBLICATIONS

Reid, M.E. and Lomas–Francis, C., *The Blood Group Antigen Facts Book*, Academic Press, San Diego, CA pp. 19–26, 251–254 (1997).

Ellis, N.A. et al., "Cloning of PBDX, an MIC2–related gene that spans the pseudoautosomal boundary on chromosome Xp", *Nat. Genet.* 6: 394–399 (1994).

Ellis, N.A. et al., "PBDX is the XG blood group gene", *Nat. Genet.* 8: 285–289 (1994).

van Driel, I.R. et al., "Murine plasma cell membrane antigen PC–1: Molecular cloning of cDNA and analysis of expression", *Proc. Natl. Acad. Sci. USA* 82: 8619–8623 (1985).

Buckley, M.F. et al., "Plasma Cell Membrane Glycoprotein PC–1", *J. Biol. Chem.* 265: 17506–17511 (1990).

Belli, S.I. et al., "Identification and characterization of a soluble form of the plasma cell membrane glycoprotein PC–1 (5'–nucleotide phosphodiesterase)", *Eur. J. Biochem.* 217: 421–428 (1993).

Funakoshi, I. et al., "Molecular cloning of cDNAs for human fibroblast nucleotide pyrophospatase", *Arch. Biochem. Biophys.* 295: 180–187 (1992).

Rebbe, N.F. et al., "Identification of nucleotide pyrophosphatase/alkaline phosphodiesterase I activity associated with the mouse plasma cell differentiation antigen PC–1", *Proc. Natl. Acad. Sci. USA* 88: 5192–5196 (1991).

Goding, J.W. et al., "Ecto–phosphodiesterase/pyrophospatase of lymphocytes and non–lymphoid cells: structure and function of the PC–1 family", *Immunol. Rev.* 161: 11–26 (1998).

Ellis, N.A. et al., (Direct Submission), GenBank Sequence Database (Accession 2499136), National Center for Biotechnology Information, National Library of Medicine, Bethesda, Maryland, 20894 (GI 2499136) Nov. 1, 1997.

Whitfield, L.S., (Direct Submission), GenBank Sequence Database (Accession X96421), National Center for Biotechnology Information, National Library of Medicine, Bethesda, Maryland, 20894 (GI 1216157) Jun. 25, 1997.

Buckley, M.F. et al., (Direct Submission), GenBank Sequence Database (Accession 189650), National Center for Biotechnology Information, National Library of Medicine, Bethesda, Maryland, 20894 (GI 189650) Mar. 7, 1995.

Buckley, M.F. et al., (Direct Submission), GenBank Sequence Database (Accession M57736 J05654), National Center for Biotechnology Information, National Library of Medicine, Bethesda, Maryland, 20894 (GI 189649) Mar. 7, 1995.

de la Fuente, M.A. et al., "CD84 Leukocyte Antigen Is a New Member of the Ig Superfamily", *Blood* 90(6): 2398–2405 (1997).

*Primary Examiner*—Karen Cochrane Carlson
*Assistant Examiner*—Devesh Srivastava
*Attorney, Agent, or Firm*—Colette C. Muenzen; Incyte Pharmaceuticals, Inc.

[57] ABSTRACT

The invention provides human cell surface glycoproteins (CSGP) and polynucleotides which identify and encode CSGP. The invention also provides expression vectors, host cells, antibodies, agonists, and antagonists. The invention also provides methods for diagnosing, treating, or preventing disorders associated with expression of CSGP.

9 Claims, 10 Drawing Sheets

```
                  11          20          29          38          47          56
  5' GAGAG AAT AGC TAC AGA TTC TCC ATC CTC AGT CTT TGC AAG GCG ACA GCT GTG CCA 65          74          83          92         101         110
      GCC GGG CTC TGG CAG GCT CCT GGC AGC ATG GCA GTG AAG CTT GGG ACC CTC CTG
                                            M   A   V   K   L   G   T   L   L 119         128         137         146         155         164
      CTG GCC CTT GCC CTG GGC CTG GCC CAG CCA GCC TCT GCC CGC CGG AAG CTG CTG
       L   A   L   A   L   G   L   A   Q   P   A   S   A   R   R   K   L   L 173         182         191         200         209         218
      GTG TTT CTG CTG GAT GGT TTT CGC TCA GAC TAC ATC AGT GAT GAG GCG CTG GAG
       V   F   L   L   D   G   F   R   S   D   Y   I   S   D   E   A   L   E 227         236         245         254         263         272
      TCA TTG CCT GGT TTC AAA GAG ATT GTG AGC AGG GGA GTA AAA GTG GAT TAC TTG
       S   L   P   G   F   K   E   I   V   S   R   G   V   K   V   D   Y   L 281         290         299         308         317         326
      ACT CCA GAC TTC CCT AGT CTC TCG TAT CCC AAT TAT TAT ACC CTA ATG ACT GGC
       T   P   D   F   P   S   L   S   Y   P   N   Y   Y   T   L   M   T   G 335         344         353         362         371         380
      CGC CAT TGT GAA GTC CAT CAG ATG ATC GGG AAC TAC ATG TGG GAC CCC ACC ACC
       R   H   C   E   V   H   Q   M   I   G   N   Y   M   W   D   P   T   T
```

```
                   11           20           29           38           47           56
5' TGCAG ATT GGT TGG GGC AGC CCG GGG AGG CTG GCT CCG ACA CAC GAC TGA GTG TGC 65           74           83           92          101          110
   CTA CAC TGG TCC CAC AGG TTT TCA GCT GTG GAG TTT GGG ATC TGA GCT TGG AGC 119          128          137          146          155          164
   CCA TTT GTT TCT GGC AGT TCC GCT CAT ATT TTC CAC TTG AAG ACA TCG CCT CCC 173          182          191          200          209          218
   TTC CTT CCA AGC TGG GAG ACC AGA AGT CAA CAA CAG GAG GGT GGA GAG GCC GGG 227          236          245          254          263          272
   TCT CAC AAT CCG GGC TGG GGA GTC CAC TGA GGT TCT TGC ATC CTG AAG CAA 281          290          299          308          317          326
   ACC ATG GAG AGC TGG TGG GGA CTT CCC TGT CTT GCG TTC CTG TGT TTT CTA ATG
       M   E   S   W   W   G   L   P   C   L   A   F   L   C   F   L   M 335          344          353          362          371          380
   CAC GCC CGA GGT CAA AGA GAC TTT GAT TTG GCA GAT GCC CTT GAT GAC CCT GAA
       H   A   R   G   Q   R   D   F   D   L   A   D   A   L   D   D   P   E 389          398          407          416          425          434
   CCC ACC AAG AAG CCA AAC TCA GAT ATC TAC CCA AAG CCA AAA CCA CCT TAC TAC
       P   T   K   K   P   N   S   D   I   Y   P   K   P   K   P   P   Y   Y

FIGURE 1A
```

```
     443        452        461        470        479        488
CCA CAG CCC GAG AAT CCC GAC AGC GGT GGA AAT ATC TAC CCA AGG CCA AAG CCA
 P   Q   P   E   N   P   D   S   G   G   N   I   Y   P   R   P   K   P 497        506        515        524        533        542
CGC CCT CAA CCC CAG CCT GGC AAT TCC GGC AAC AGT GGA GGT TAC TTC AAT GAT
 R   P   Q   P   Q   P   G   N   S   G   N   S   G   G   Y   F   N   D 551        560        569        578        587        596
GTG GAC CGT GAT GAC GGA CGC TAC TCC CCC AGG CCA CGG CCA GGT CCT GCA
 V   D   R   D   D   G   R   Y   S   P   R   P   R   P   G   P   P   A 605        614        623        632        641        650
GGA GGT GGC GGT TAT GGC TAT TCC AGT TAT GGC AAC TCC GAC AGG CCA CGG CCA CAC
 G   G   G   G   Y   G   Y   S   S   Y   G   N   S   D   R   P   R   P   H 659        668        677        686        695        704
AGA GGG GGC TAT AGA CCC AAC TCT CGT TAT GGA AAT ACT TAT GGT GGA GAT CAC
 R   G   G   Y   R   P   N   S   R   Y   G   N   T   Y   G   G   D   H 713        722        731        740        749        758
CAT TCA ACG TAT GGC AAT CCA GAA GGC AAT ATG GTA GCA AAA ATC GTG TCT CCC
 H   S   T   Y   G   N   P   E   G   N   M   V   A   K   I   V   S   P 767        776        785        794        803        812
ATC GTA TCC GTG GTG GTG ACA CTG CTG GGA GCA GCA GCC AGT TAT TTC AAA
 I   V   S   V   V   V   T   L   L   G   A   A   A   S   Y   F   K
```

FIGURE 1B

```
     821         830         839     848         857         866
CTA AAC AAT AGG AGA AAT TGT TTC AGG ACC CAT GAA CCA GAA AAT GTC TGA AGA
 L   N   N   R   R   N   C   F   R   T   H   E   P   E   N   V   *
     875         884         893     902         911         920
TGT TAA GAT CCC CTG ATT ACT TTG GGA AAA ACA ACT AAA ACA AGA ACC GTG TTT
     929
ATC AAA AAA AAA AAA 3'
```

FIGURE 1C

| | | |
|---|---|---|
| 1 | M E S W W G L P C L A F L C F L M H A R G Q R D F D L A D A | 2297891 |
| 1 | M E S W W G L P C L A F L C F L M H A R G Q R D F D L A D A | GI 2499136 |
| 31 | L D D P E P T K K P N S D I Y P K P K P P Y Y P Q P E N P D | 2297891 |
| 31 | L D D P E P T K K P N S D I Y P K P K P P Y Y P Q P E N P D | GI 2499136 |
| 61 | S G G N I Y P R P K P R P Q P Q P G N S G G Y F N D V | 2297891 |
| 61 | S G G N I Y P R P K P R P Q P Q P G N S G G Y F N D V | GI 2499136 |
| 91 | D R D D G R Y P P R P R P R P P A G G G G G Y S S Y G N S | 2297891 |
| 91 | D R D D G R Y P P R P R P R P P A G G G G G Y S S Y G N S | GI 2499136 |
| 121 | D N T H G R G G Y R P N S R Y G N T Y G G D H H S T Y G N P | 2297891 |
| 121 | D N T H G - - - - - - - - - - - G D H H S T Y G N P | GI 2499136 |
| 151 | E G N M V A K I V S P I V S V V V T L L G A A A S Y F K L | 2297891 |
| 136 | E G N M V A K I V S P I V S V V V T L L G A A A S Y F K L | GI 2499136 |
| 181 | N N R R N C F R T H E P E N V | 2297891 |
| 166 | N N R R N C F R T H E P E N V | GI 2499136 |

FIGURE 2

FIGURE 3A

```
5' GAGAG  AAT AGC TAC AGA  TTC TCC ATC CTC  AGT CTT TGC AAG  GCG ACA GCT GTG  CCA
         11              20               29               38               47           56

GCC GGG CTC TGG  CAG GCT CCT GGC  AGC ATG GCA GTG  AAG CTT GGG ACC  CTC CTG
                                              M   A   V    K   L   G   T    L   L
   65               74               83               92              101          110

CTG GCC CTT GCC  CTG GGC CTG GCC  ATG GCA CCA GCC  AAG CTT GCC CGC  TCT GCC CGC  AAG CTG CTG
    L   A   L   A   L   G   L   A    M   A   P   A    K   L   A   R    S   A   R    K   L   L
   119             128              137              146              155          164

GTG TTT CTG GAT  GGT TTT CGC AGC  TCA GAC TAC ATC  AGT GAT GAG GCG  CTG GAG
    V   F   L   D   G   F   R   S    S   D   Y   I    S   D   E   A    L   E
   173             182              191              200              209          218

TCA TTG CCT GGT  TTC AAA GAG ATT  GTG AGC AGG GGA  GTA AAA GTG GAT  TAC TTG
    S   L   P   G   F   K   E   I    V   S   R   G    V   K   V   D    Y   L
   227             236              245              254              263          272

ACT CCA GAC TTC  CCT AGT CTC TCG  TAT CCC AAT TAT  ACC CTA ATG ACT  GGC
    T   P   D   F   P   S   L   S    Y   P   N   Y    T   L   M   T    G
   281             290              299              308              317          326

CGC CAT TGT GAA  GTC CAT CAG ATG  ATC GGG AAC TAC  ATG TGG GAC CCC  ACC ACC
    R   H   C   E   V   H   Q   M    I   G   N   Y    M   W   D   P    T   T
   335             344              353              362              371          380
```

```
        389 TCC TTT GAC ATT GGC GTC AAC AAA GAC AGC CTA ATG CCT CTC TGG 434
AAC AAG  S   F   D   I   G   V   N   K   D   S   L   M   P   L   W
 N   K

443 TCA GAA CCT CTG TGG GTC ACT CTG ACC AAG GCC AAA AGG AAG GTC TAC 488
AAT GGA  S   E   P   L   W   V   T   L   T   K   A   K   R   K   V   Y
 N   G

497 TAC TGG CCA GGC TGT GAG GTT GAG ATT CTG GGT GTC AGA CCC ACC TAC 542
ATG TAC  Y   W   P   G   C   E   V   E   I   L   G   V   R   P   T   Y
 M   Y

551 GAA TAT AAA AAT GTC CCA ACG GAT ATC AAT TTT GCC AAT GCA GTC AGC 596
TGC CTA  E   Y   K   N   V   P   T   D   I   N   F   A   N   A   V   S
 C   L

605 CTT GAC TCC TTC AAG AGT CGG GCC GAC CTG GCA CCT GCA ATA TAC CAT 650
GAT GCT  L   D   S   F   K   S   R   A   D   L   A   P   A   I   Y   H
 D   A

659 ATT GAC GTG GAA GGC CAC TAC GGG CCT GCA TCT CCG CAG AGG AAA 704
GAG CGC  I   D   V   E   G   H   Y   G   P   A   S   P   Q   R   K
 E   R

713 CTC AAG GCT GTA GAC ACT GTC CTG AAG TAC ATG ACC AAG TGG ATC CAG 758
GAT GCC  L   K   A   V   D   T   V   L   K   Y   M   T   K   W   I   Q
 D   A
```

FIGURE 3B

```
GAG CGG GGC CTG CAG GAC CGC CTG AAC GTC ATT TTC TCG GAT CAC GGA ATG
 E   R   G   L   Q   D   R   L   N   V   I   F   S   D   H   G   M
767     776     785     794         803     812

ACC GAC ATT TTC TGG ATG GAC AAA GTG CTG AAT AAG TAC ATC AGC CTG
 T   D   I   F   W   M   D   K   V   L   N   K   Y   I   S   L
821     830     839         848     857     866

AAT GAC CTG CAG CAA AAG GAC GTG ATT GAG ATT CGC GGG CCT GTT GTG AGC GCC
 N   D   L   Q   Q   K   D   V   I   E   I   R   G   P   V   V   S   A
875     884     893         902     911     920

CCT GGG AAA CAC TCT GAG ATA TAT AAC AAA CTG AGC ACA GTG GAA CAC ATG ACT
 P   G   K   H   S   E   I   Y   N   K   L   S   T   V   E   H   M   T
929     938         947     956     965     974

GTC TAC GAG AAA GAA GCC ATC CCA AGC AGG TTC TAT TAC AAG AAA GGA AAG TTT
 V   Y   E   K   E   A   I   P   S   R   F   Y   Y   K   K   G   K   F
983         992     1001    1010    1019    1028

GTC TCT CCT TTG ACT TTA GTG GCT GAT GAA GGC TGG TTC ATA ACT GAG AAT CGA
 V   S   P   L   T   L   V   A   D   E   G   W   F   I   T   E   N   R
1037    1046        1055    1064    1073    1082

GAG ATG CTT CCG TTT TGG ATG AAC AGC ACC GGC AGG CGG GAA GGT TGG CAG CGT
 E   M   L   P   F   W   M   N   S   T   G   R   R   E   G   W   Q   R
1091    1100    1109    1118    1127    1136
```

FIGURE 3C

```
        1145            1154            1163            1172            1181            1190
GGA TGG CAC GGC TAC GAC AAC GAG CTC ATG GAC ATG CGG GGC ATC TTC CTG ACT
 G   W   H   G   Y   D   N   E   L   M   D   M   R   G   I   F   L   T
        1199            1208            1217            1226            1235            1244
CTC GGA CCT GGT AGG CGA GGA AAT CAG ATG GAC CTC TCA GAC CCC ATT CCC AAG
 L   G   P   G   R   R   G   N   Q   M   D   L   S   D   P   I   P   K
        1253            1262            1271            1280            1289            1298
GAA GTG TCT CTA AGG GGC CCT ACG GGT GCC AGG AGA GGC TGC AGG GAT TTC CTC
 E   V   S   L   R   G   P   T   G   A   R   R   G   C   R   D   F   L
        1307            1316            1325            1334            1343            1352
ACA GAC CCT CTT TAT GAG CCA AGC AGA GCA AAC CCA GCC GGT CTC CAT GAA ACA
 T   D   P   L   Y   E   P   S   R   A   N   P   A   G   L   H   E   T
        1361            1370            1379            1388            1397            1406
TCT TTT GCT GGC TTC CTT TCA AAT GCT TCT TGG GTT TGG CAA ATG TAG CCA AAT
 S   F   A   G   F   L   S   N   A   S   W   V   W   Q   M   *
        1415            1424            1433
ACT GTG CCG TGT AAA TTT TAA ATC CTG CAG CA 3'
```

FIGURE 3D

|     |                                                             |          |
| --- | ----------------------------------------------------------- | -------- |
| 27  | L V F L L D G F R S D Y I S D - E A L E S L P G F K E I V S | 2705267  |
| 161 | L L F S L D G F R A E Y L H T W G G L - - L P V I S K L K K | GI 189650 |
|     |                                                             |          |
| 56  | R G V K V D Y L T P D F P S L S Y P N Y Y T L M T G R H C E | 2705267  |
| 189 | C G T Y T K N M R P V Y P T K T F P N H Y S I V T G L Y P E | GI 189650 |
|     |                                                             |          |
| 86  | V H Q M I G N Y M W D P T T N K S F D I G V N K D S L M P L | 2705267  |
| 219 | S H G I I D N K M Y D P K M N A S F S L K - S K E K F N P E | GI 189650 |
|     |                                                             |          |
| 116 | W N N G S E P L W V T L T K A K R K V Y M Y Y W P G C E V E | 2705267  |
| 248 | W Y K G - E P I W V T A K Y Q G L K S G T F F W P G S D V E | GI 189650 |
|     |                                                             |          |
| 146 | I L G V R P T Y C L E Y K N V P T D I N F A N A V S D A L D | 2705267  |
| 277 | I N G I F P D I - - - Y K M Y N G S V P F E E R I L A V L Q | GI 189650 |
|     |                                                             |          |
| 176 | S F - - - K S G R A D L A A I Y H E R I D V E G H H Y G P A | 2705267  |
| 304 | W L Q L P K D E R P H F Y T L Y L E E P D S S G H S Y G P V | GI 189650 |
|     |                                                             |          |
| 203 | S P Q R K D A L K A V D T V L K Y M T K W I Q E R G L Q D R | 2705267  |
| 334 | S S E V I K A L Q R V D G M V G M L M D G L K E L N L H R C | GI 189650 |

CELL SURFACE GLYCOPROTEINS

FIELD OF THE INVENTION

This invention relates to nucleic acid and amino acid sequences of cell surface glycoproteins and to the use of these sequences in the diagnosis, treatment, and prevention of hematologic, karyotypic, and neuronal disorders.

BACKGROUND OF THE INVENTION

Proteins expressed on the cell surface function as stage-specific markers of cell differentiation and as antigenic determinants for immunological identification of distinct cell types. In the context of tissue construction and intercellular communication, cell surface proteins play critical roles in cell-cell recognition and adhesion, cell motility, and signal transduction. Cell surface proteins are anchored to the plasma membrane by one or more membrane-spanning domains or by covalent attachment to lipophilic membrane-embedded molecules such as glycosylphosphatidylinositol. Most cell surface proteins are synthesized as immature, inactive precursors which require post-translational modifications for activity. Such modifications include proteolytic processing, glycosylation, oligomerization, and disulfide bond formation. Proteins destined for the cell surface generally contain N-terminal signal peptides which are cleaved from the mature protein.

Blood group antigens are immunologically defined marker proteins found on the surface of red blood cells. These markers provide a means for classification of blood group systems. For example, the most commonly known blood group system is defined by the A, B, and O antigens. The particular antigen(s) expressed by a given individual is determined by the allele, or variant, of the ABO gene that the individual has inherited. The blood type of the individual is therefore defined by the serologically expressed antigen(s). The implications of the ABO system on blood transfusion practice are well known. In addition, the A and B antigens have potential application in the diagnosis of blood disorders such as leukemia, thalassemia, and anemia which weaken the expression of these antigens. (Reviewed in Reid, M. E. and Lomas-Francis, C. (1997) *The Blood Group Antigen Facts Book*, Academic Press, San Diego, Calif., pp. 19–26.)

Although the ABO system is well known for its clinical relevance, other blood group systems exist. One such blood group system is the XG system which is defined by a single antigen, $Xg^a$. $Xg^a$ is encoded by one of two allelic forms of the XG gene. The other XG allele fails to encode a detectable gene product. (Reviewed in Reid and Lomas-Francis, supra, pp. 251–254.) The XG gene is situated on the X chromosome at the boundary between the pseudoautosomal, or X-specific, region and the region which has homology to Y chromosome sequences. (Ellis, N. A. et al. (1994) Nat. Genet. 6:394–399.) The latter region is particularly important for recombination between the X and Y chromosomes during male meiosis. Lack of recombination results in the failure of X and Y to segregate and ultimately leads to the generation of male progeny with an XXY karyotype. XXY individuals suffer from Klinefelter syndrome, a complex developmental disorder characterized by infertility, gynecomastia and other manifestations of feminization, increased height, obesity, mental deficiency, thyroid abnormalities, diabetes, pulmonary disease, and increased risk of breast cancer.

The XG gene has been cloned and sequenced (Ellis, supra, and Ellis, N. A. et al. (1994) Nat. Genet. 8:285–289). XG RNA is detectable at low levels in fibroblasts and in some bone marrow preparations. XG cDNA predicts a proline- and glycine-rich protein of 180 amino acids with an N-terminal signal peptide. A transmembrane domain from amino acid 88 through 116 separates the N-terminal extracellular domain from the C-terminal intracellular domain. The XG protein may play a role in cell adhesion.

The surface of white blood cells, like that of red blood cells, is populated with characteristic glycoproteins. For example, the plasma cell glycoprotein-1 (PC-1) is expressed on the surface of plasma cells, which are terminally differentiated, antibody-secreting B-lymphocytes. PC-1 is also expressed in nonlymphoid tissue such as kidney, chondrocytes, epididymis, and hepatocytes. PC-1 was initially isolated from murine plasma cells as a homodimer with subunits of 115 kilodaltons each (van Driel, I. R. et al. (1985) Proc. Natl. Acad. Sci. USA 82:8619–8623). Biochemical and immunological analyses have suggested that murine PC-1 (mPC-1) is expressed in neuroblastomas. However, molecular analyses failed to confirm this observation, suggesting that neuroblastoma tissue contains a glycoprotein having biochemical similarity to or immunological cross-reactivity with mPC-1. mPC-1 cDNA encodes a predicted protein of 871 amino acids with a short N-terminal cytoplasmic domain, a single transmembrane domain, and a large C-terminal extracellular domain of 826 amino acids. Human PC-1 (hPC-1) is 873 amino acids in length and 80% identical to the mouse protein (Buckley, M. F. et al. (1990) J. Biol. Chem. 265:17506–17511). hPC-1 possesses the same overall domain structure as mPC-1. In addition, a soluble form of mPC-1 has been found in serum and other extracellular fluids (Belli, S. I. et al. (1993) Eur. J. Biochem. 217:421–428). This soluble form of mPC-1 likely results from proteolytic cleavage which frees most of the extracellular domain from the transmembrane domain.

The extracellular domains of both hPC-1 and mPC-1 have nucleotide phosphodiesterase (pyrophosphatase) activity (Funakoshi, I. et al. (1992) Arch. Biochem. Biophys. 295:180–187; Rebbe, N. F. et al. (1991) Proc. Natl. Acad. Sci. USA 88:5192–5196). In hPC-1, the enzymatic active site for this activity likely occurs within the region from amino acids 166 through 225. Phosphodiesterase activity is associated with the hydrolytic removal of nucleotide subunits from oligonucleotides. Although the precise physiological roles of hPC-1 and mPC-1 are not clear, increased hPC-1 phosphodiesterase activity has been correlated with insulin resistance in patients with noninsulin-dependent diabetes mellitus, with abnormalities of bone mineralization and calcification, and with defects in renal tubule function. In addition, it appears that hPC-1 and mPC-1 are members of a multigene family of transmembrane phosphodiesterases with extracellular active sites. These enzymes may play a role in regulating the concentration of pharmacologically active extracellular compounds such as adenosine or other nucleotide derivatives in a variety of tissues and cell types. (Reviewed in Goding, J. W. et al. (1998) Immunol. Rev. 161:11–26.)

The discovery of new cell surface glycoproteins and the polynucleotides encoding them satisfies a need in the art by providing new compositions which are useful in the diagnosis, prevention, and treatment of hematologic, karyotypic, and neuronal disorders.

SUMMARY OF THE INVENTION

The invention features substantially purified polypeptides, cell surface glycoproteins, referred to collectively as "CSGP" and individually as "CSGP-1" and "CSGP-2". In one aspect, the invention provides a substantially purified polypeptide comprising an amino acid sequence selected from the group consisting of SEQ ID NO:1, SEQ ID NO:2, and fragments thereof.

The invention further provides a substantially purified variant having at least 90% amino acid identity to at least one of the amino acid sequences selected from the group consisting of SEQ ID NO:1, SEQ ID NO:2, and fragments thereof. The invention also provides an isolated and purified polynucleotide encoding the polypeptide comprising an amino acid sequence selected from the group consisting of SEQ ID NO:1, SEQ ID NO:2, and fragments thereof. The invention also includes an isolated and purified polynucleotide variant having at least 90% polynucleotide sequence identity to the polynucleotide encoding the polypeptide comprising an amino acid sequence selected from the group consisting of SEQ ID NO:1, SEQ ID NO:2, and fragments thereof.

Additionally, the invention provides an isolated and purified polynucleotide which hybridizes under stringent conditions to the polynucleotide encoding the polypeptide comprising an amino acid sequence selected from the group consisting of SEQ ID NO:1, SEQ ID NO:2, and fragments thereof. The invention also provides an isolated and purified polynucleotide having a sequence which is complementary to the polynucleotide encoding the polypeptide comprising the amino acid sequence selected from the group consisting of SEQ ID NO:1, SEQ ID NO:2, and fragments thereof.

The invention also provides an isolated and purified polynucleotide comprising a polynucleotide sequence selected from the group consisting of SEQ ID NO:3, SEQ ID NO:4, and fragments thereof. The invention further provides an isolated and purified polynucleotide variant having at least 90% polynucleotide sequence identity to the polynucleotide sequence selected from the group consisting of SEQ ID NO:3, SEQ ID NO:4, and fragments thereof. The invention also provides an isolated and purified polynucleotide having a sequence which is complementary to the polynucleotide comprising a polynucleotide sequence selected from the group consisting of SEQ ID NO:3, SEQ ID NO:4, and fragments thereof.

The invention also provides a method for detecting a polynucleotide in a sample containing nucleic acids, the method comprising the steps of (a) hybridizing the complement of the polynucleotide sequence to at least one of the polynucleotides of the sample, thereby forming a hybridization complex; and (b) detecting the hybridization complex, wherein the presence of the hybridization complex correlates with the presence of a polynucleotide in the sample. In one aspect, the method further comprises amplifying the polynucleotide prior to hybridization.

The invention further provides an expression vector containing at least a fragment of the polynucleotide encoding the polypeptide comprising an amino acid sequence selected from the group consisting of SEQ ID NO:1, SEQ ID NO:2, and fragments thereof. In another aspect, the expression vector is contained within a host cell.

The invention also provides a method for producing a polypeptide, the method comprising the steps of: (a) culturing the host cell containing an expression vector containing at least a fragment of a polynucleotide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1, SEQ ID NO:2, and fragments thereof, in conjunction with a suitable pharmaceutical carrier.

The invention further includes a purified antibody which binds to a polypeptide selected from the group consisting of SEQ ID NO:1, SEQ ID NO:2, and fragments thereof. The invention also provides a purified agonist and a purified antagonist to the polypeptide.

The invention also provides a method for treating or preventing a disorder associated with decreased expression or activity of CSGP, the method comprising administering to a subject in need of such treatment an effective amount of a pharmaceutical composition comprising a substantially purified polypeptide having the amino acid sequence selected from the group consisting of SEQ ID NO:1, SEQ ID NO:2, and fragments thereof, in conjunction with a suitable pharmaceutical carrier.

The invention also provides a method for treating or preventing a disorder associated with increased expression or activity of CSGP, the method comprising administering to a subject in need of such treatment an effective amount of an antagonist of a polypeptide having an amino acid sequence selected from the group consisting of SEQ ID NO:1, SEQ ID NO:2, and fragments thereof.

BRIEF DESCRIPTION OF THE FIGURES AND TABLE

FIGS. 1A, 1B, and 1C show the amino acid sequence (SEQ ID NO:1) and nucleic acid sequence (SEQ ID NO:3) of CSGP-1. The alignment was produced using MACDNASIS PRO software (Hitachi Software Engineering, South San Francisco Calif.).

FIG. 2 shows the amino acid sequence alignment between CSGP-1 (2297891; SEQ ID NO:1) and human XG (GI 2499136; SEQ ID NO:5). The alignment was produced using the multisequence alignment program of LASERGENE software (DNASTAR, Madison Wis.).

FIGS. 3A, 3B, 3C, and 3D show the amino acid sequence (SEQ ID NO:2) and nucleic acid sequence (SEQ ID NO:4) of CSGP-2.

FIGS. 4A and 4B show the amino acid sequence alignment between amino acid residues 27 through 378 of CSGP-2 (2705267; SEQ ID NO:2) and amino acid residues 161 through 508 of hPC-1 (GI 189650; SEQ ID NO:6).

Table 1 shows the programs, their descriptions, references, and threshold parameters used to analyze CSGP.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

DEFINITIONS

"CSGP" refers to the amino acid sequences of substantially purified CSGP obtained from any species, particularly a mammalian species, including bovine, ovine, porcine, murine, equine, and preferably the human species, from any source, whether natural, synthetic, semi-synthetic, or recombinant.

The term "agonist" refers to a molecule which, when bound to CSGP, increases or prolongs the duration of the effect of CSGP. Agonists may include proteins, nucleic acids, carbohydrates, or any other molecules which bind to and modulate the effect of CSGP.

An "allelic variant" is an alternative form of the gene encoding CSGP. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding CSGP include those sequences with deletions, insertions, or substitutions of different nucleotides, resulting in a polynucleotide the same as CSGP or a polypeptide with at least one functional characteristic of CSGP. Included within this definition are polymorphisms which may or may not be readily detectable using a particular oligonucleotide probe of the polynucleotide encoding CSGP, and improper or unexpected hybridization to allelic variants, with a locus other than the normal chromosomal locus for the polynucleotide sequence encoding CSGP. The encoded protein may also be "altered," and may contain deletions, insertions, or substitutions of amino acid residues which produce a silent change and result in a functionally equivalent CSGP. Deliberate amino acid substitutions may be made on the basis of similarity in polarity, charge, solubility, hydrophobicity, hydrophilicity, and/or the amphipathic nature of the residues, as long as the biological or immunological activity of CSGP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence" refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of CSGP which are preferably at least 5 to about 15 amino acids in length, most preferably at least 14 amino acids, and which retain some biological activity or immunological activity of CSGP. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which, when bound to CSGP, decreases the amount or the duration of the effect of the biological or immunological activity of CSGP. Antagonists may include proteins, nucleic acids, carbohydrates, antibodies, or any other molecules which decrease the effect of CSGP.

The term "antibody" refers to intact molecules as well as to fragments thereof, such as Fab, $F(ab')_2$, and Fv fragments, which are capable of binding the epitopic determinant. Antibodies that bind CSGP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The term "biologically active," refers to a protein having structural, regulatory, or biochemical functions of a naturally occurring molecule. Likewise, "immunologically active" refers to the capability of the natural, recombinant, or synthetic CSGP, or of any oligopeptide thereof, to induce a specific immune response in appropriate animals or cells and to bind with specific antibodies.

The terms "complementary" or "complementarity" refer to the natural binding of polynucleotides by base pairing. For example, the sequence "5' A-G-T 3'" bonds to the complementary sequence "3' T-C-A 5'."Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence" refer broadly to any composition containing the given polynucleotide or amino acid sequence. The composition may comprise a dry formulation or an aqueous solution. Compositions comprising polynucleotide sequences encoding CSGP or fragments of CSGP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been resequenced to resolve uncalled bases, extended using XL-PCR kit (Perkin-Elmer, Norwalk Conn.) in the 5' and/or the 3' direction, and resequenced, or which has been assembled from the overlapping sequences of more than one Incyte Clone using a computer program for fragment assembly, such as the GELVIEW fragment assembly system (GCG, Madison Wis.). Some sequences have been both extended and assembled to produce the consensus sequence.

The term "correlates with expression of a polynucleotide" indicates that the detection of the presence of nucleic acids, the same or related to a nucleic acid sequence encoding CSGP, by northern analysis is indicative of the presence of nucleic acids encoding CSGP in a sample, and thereby correlates with expression of the transcript from the polynucleotide encoding CSGP.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity" refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Madison Wis.) which creates alignments between two or more sequences according to methods selected by the user, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid binds with a complementary strand through base pairing.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition" refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray" refers to an arrangement of distinct polynucleotides on a substrate.

The terms "element" or "array element" in a microarray context, refer to hybridizable polynucleotides arranged on the surface of a substrate.

The term "modulate" refers to a change in the activity of CSGP. For example, modulation may cause an increase or a decrease in protein activity, binding characteristics, or any other biological, functional, or immunological properties of CSGP.

The phrases "nucleic acid" or "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked" refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. "Oligonucleotide" is substantially equivalent to the terms "amplimer," "primer," "oligomer," and "probe," as these terms are commonly defined in the art.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

The term "sample" is used in its broadest sense. A sample suspected of containing nucleic acids encoding CSGP, or fragments thereof, or CSGP itself, may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of CSGP polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to CSGP. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

THE INVENTION

The invention is based on the discovery of new human cell surface glycoproteins (CSGP), the polynucleotides encoding CSGP, and the use of these compositions for the diagnosis, treatment, or prevention of hematologic, karyotypic, and neuronal disorders.

Nucleic acids encoding the CSGP-1 of the present invention were identified in Incyte Clone 2297891H1 from the breast tissue cDNA library (BRSTNOT05) using a computer search for nucleotide and/or amino acid sequence alignments. A consensus sequence, SEQ ID NO:3, was derived from the following overlapping and/or extended nucleic acid sequences: Incyte Clones 2297891H1 and 2297891R6 (BRSTNOT05), 727622H1 (SYNOOAT01), and shotgun sequences SAXA00975F1 and SAXA00091F1.

In one embodiment, the invention encompasses a polypeptide comprising the amino acid sequence of SEQ ID NO:1, as shown in FIG. 1A, 1B, and 1C. CSGP-1 is 195 amino acids in length and has one potential protein kinase C phosphorylation site at T37. HMM and SPSCAN analyses predict a signal peptide in CSGP-1 from M1 to G21. As shown in FIG. 2, CSGP-1 has significant amino acid identity with human XG (GI 2499136; SEQ ID NO:5). However, CSGP-1 contains a region of unique amino acid sequence from R126 to G140, suggesting that CSGP-1 is generated by alternative splicing of XG-encoded RNA. Fragments of SEQ ID NO:3 from about nucleotide 246 to about nucleotide 275 and from about nucleotide 651 to about nucleotide 695 are useful in hybridization or amplification technologies to identify SEQ ID NO:3 and to distinguish between SEQ ID NO:3 and a related sequence. Northern analysis shows the expression of this sequence in seven cDNA libraries, three of which are associated with vascular tissue.

Nucleic acids encoding the CSGP-2 of the present invention were identified in Incyte Clone 2705267H1 from the diseased brain tissue cDNA library (PONSAZT01) using a computer search for nucleotide and/or amino acid sequence alignments. A consensus sequence, SEQ ID NO:4, was derived from the following overlapping and/or extended nucleic acid sequences: Incyte Clones 2705267H1 and 2705267T6 (PONSAZT01), 3347532H1 (BRAITUT24), and shotgun sequences SBDA02672F1 and SBDA04322F1.

In one embodiment, the invention encompasses a polypeptide comprising the amino acid sequence of SEQ ID NO:2, as shown in FIGS. 3A, 3B, 3C, and 3D. CSGP-2 is 438 amino acids in length and has four potential N-glycosylation sites at N 100, N 118, N341, and N431; three potential casein kinase II phosphorylation sites at S260, S291, and T297; seven potential protein kinase C phosphorylation sites at S21, T80, T99, S 176, S 179, T343, and S390; and two potential tyrosine kinase phosphorylation sites at Y199 and Y258. HMM and SPSCAN analyses predict a signal peptide in CSGP-2 from M1 to A17 or A22. CSGP-2 has chemical and structural similarity with hPC-1 (GI 189650; SEQ ID NO:6). As shown in FIGS. 4A and 4B, the region of CSGP-2 from L27 through D378 shares 26% identity with the extracellular region of hPC-1 from L161 through E508. In particular, the region of CSGP-2 from D32 through N92 shares 33% identity with the active site region of hPC-1 from D166 through N225. In addition, the potential N-glycosylation sites at N100 and N341 and the potential phosphorylation sites at S291 and T343 in CSGP-2 are conserved in hPC-1. Fragments of SEQ ID NO:4 from about nucleotide 150 to about nucleotide 179 and from about nucleotide 228 to about nucleotide 275 are useful in hybridization or amplification technologies to identify SEQ ID NO:4 and to distinguish between SEQ ID NO:4 and a related sequence. Northern analysis shows the expression of this sequence in eight cDNA libraries, all of which are derived from brain tissue, including tumorous and Alzheimer's brain tissue.

The invention also encompasses CSGP variants. A preferred CSGP variant is one which has at least about 80%, more preferably at least about 90%, and most preferably at least about 95% amino acid sequence identity to the CSGP amino acid sequence, and which contains at least one functional or structural characteristic of CSGP.

The invention also encompasses polynucleotides which encode CSGP. In a particular embodiment, the invention encompasses a polynucleotide sequence comprising a sequence selected from the group consisting of SEQ ID NO:3 and SEQ ID NO:4, which encodes CSGP.

The invention also encompasses a variant of a polynucleotide sequence encoding CSGP. In particular, such a variant polynucleotide sequence will have at least about 80%, more preferably at least about 90%, and most preferably at least about 95% polynucleotide sequence identity to the polynucleotide sequence encoding CSGP. A particular aspect of the invention encompasses a variant of a polynucleotide sequence comprising a sequence selected from the group consisting of SEQ ID NO:3 and SEQ ID NO:4 which has at least about 80%, more preferably at least about 90%, and most preferably at least about 95% polynucleotide sequence identity to a nucleic acid sequence selected from the group consisting of SEQ ID NO:3 and SEQ ID NO:4. Any one of the polynucleotide variants described above can encode an amino acid sequence which contains at least one functional or structural characteristic of CSGP.

It will be appreciated by those skilled in the art that as a result of the degeneracy of the genetic code, a multitude of polynucleotide sequences encoding CSGP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring CSGP, and all such variations are to be considered as being specifically disclosed.

Although nucleotide sequences which encode CSGP and its variants are preferably capable of hybridizing to the nucleotide sequence of the naturally occurring CSGP under appropriately selected conditions of stringency, it may be advantageous to produce nucleotide sequences encoding CSGP or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding CSGP and its derivatives without altering the encoded amino acid sequences include the production of RNA transcripts having more desirable properties, such as a greater half-life, than transcripts produced from the naturally occurring sequence.

The invention also encompasses production of DNA sequences which encode CSGP and CSGP derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding CSGP or any fragment thereof.

Also encompassed by the invention are polynucleotide sequences that are capable of hybridizing to the claimed polynucleotide sequences, and, in particular, to those shown in SEQ ID NO:3 and SEQ ID NO:4 and fragments thereof under various conditions of stringency. (See, e.g., Wahl, G. M. and S. L. Berger (1987) Methods Enzymol. 152:399–407; Kimmel, A. R. (1987) Methods Enzymol. 152:507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μ/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Perkin-Elmer), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the Hamilton MICROLAB 2200 (Hamilton, Reno Nev.), Peltier thermal cycler 200 (PTC200; MJ Research, Watertown Mass.) and the ABI CATALYST 800 (Perkin-Elmer). Sequencing is then carried out using either ABI 373 or 377 DNA sequencing systems (Perkin-Elmer) or the MEGABACE 1000 DNA sequencing system (Molecular Dynamics, Sunnyvale Calif.). The resulting sequences are analyzed using a variety of algorithms which are well known in the art. (See, e.g., Ausubel, F. M. (1997) Short Protocols in Molecular Biology, John Wiley & Sons, New York N.Y., unit 7.7; Meyers, R. A. (1995) Molecular Biology and Biotechnology, Wiley VCH, New York N.Y., pp. 856–853.)

The nucleic acid sequences encoding CSGP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin-Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode CSGP may be cloned in recombinant DNA molecules that direct expression of CSGP, or fragments or functional equivalents thereof, in appropriate host cells. Due to the inherent degeneracy of the genetic code, other DNA sequences which encode substantially the same or a functionally equivalent amino acid sequence may be produced and used to express CSGP.

The nucleotide sequences of the present invention can be engineered using methods generally known in the art in order to alter CSGP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding CSGP may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, CSGP itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431A peptide synthesizer (Perkin-Elmer). Additionally, the amino acid sequence of CSGP, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, WH Freeman, New York N.Y.)

In order to express a biologically active CSGP, the nucleotide sequences encoding CSGP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding CSGP. Such elements may vary in their strength and specificity. Specific initiation signals may also be used to achieve more efficient translation of sequences encoding CSGP. Such signals include the ATG initiation codon and adjacent sequences, e.g. the Kozak sequence. In cases where sequences encoding CSGP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding CSGP and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview N.Y., ch. 4, 8, and 16–17; Ausubel, F. M. et al. (1995) *Current Protocols in Molecular Biology*, John Wiley & Sons, New York N.Y., ch. 9, 13, and 16.)

A variety of expression vector/host systems may be utilized to contain and express sequences encoding CSGP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus,TMV) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding CSGP. For example, routine cloning, subcloning, and propagation of polynucleotide sequences encoding CSGP can be achieved using a multifunctional *E. coli* vector such as PBLUESCRIPT (Stratagene, La Jolla Calif.) or PSPORT1 plasmid (Life Technologies). Ligation of sequences encoding CSGP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of CSGP are needed, e.g. for the production of antibodies, vectors which direct high level expression of CSGP may be used. For example, vectors containing the strong, inducible T5 or T7 bacteriophage promoter may be used.

Yeast expression systems may be used for production of CSGP. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995, supra; Grant et al. (1987) Methods Enzymol. 153:516–54; and Scorer, C. A. et al. (1994) Bio/Technology 12:181–184.)

Plant systems may also be used for expression of CSGP. Transcription of sequences encoding CSGP may be driven viral promoters, e.g., the 35S and 19S promoters of CaMV used alone or in combination with the omega leader sequence from TMV (Takamatsu, N. (1987) EMBO J. 6:307–311). Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., *The McGraw Hill Yearbook of Science and Technology* (1992) McGraw Hill, New York N.Y., pp. 191–196.)

In mammalian cells, a number of viral-based expression systems may be utilized. In cases where an adenovirus is used as an expression vector, sequences encoding CSGP may be ligated into an adenovirus transcription/translation complex consisting of the late promoter and tripartite leader sequence. Insertion in a non-essential E1 or E3 region of the viral genome may be used to obtain infective virus which expresses CSGP in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat. Genet. 15:345–355.)

For long term production of recombinant proteins in mammalian systems, stable expression of CSGP in cell lines is preferred. For example, sequences encoding CSGP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in $tk^-$ or $apr^-$ cells, respectively. (See, e.g., Wigler, M. et al. (1977) Cell 11:223–232; Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides, neomycin and G-418; and als orpat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al. (1981) J. Mol. Biol. 150:1–14.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121–131.)

Although the presence/absence of marker gene expression suggests that the gene of interest is also present, the presence and expression of the gene may need to be confirmed. For example, if the sequence encoding CSGP is inserted within a marker gene sequence, transformed cells containing sequences encoding CSGP can be identified by the absence of marker gene function. Alternatively, a marker gene can be placed in tandem with a sequence encoding CSGP under the control of a single promoter. Expression of the marker gene in response to induction or selection usually indicates expression of the tandem gene as well.

In general, host cells that contain the nucleic acid sequence encoding CSGP and that express CSGP may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of CSGP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on CSGP is preferred, but a competitive binding assay may be employed. These and other assays are well known in the art. (See, e.g., Hampton, R. et al. (1990) *Serological Methods, a Laboratory Manual*, APS Press, St Paul Minn., Sect. IV; Coligan, J. E. et al. (1997) *Current Protocols in Immunology*, Greene Pub. Associates and Wiley-Interscience, New York N.Y.; and Pound, J. D. (1998) *Immunochemical Protocols*, Humana Press, Totowa N.J.).

A wide variety of labels and conjugation techniques are known by those skilled in the art and may be used in various nucleic acid and amino acid assays. Means for producing labeled hybridization or PCR probes for detecting sequences related to polynucleotides encoding CSGP include oligolabeling, nick translation, end-labeling, or PCR amplification using a labeled nucleotide. Alternatively, the sequences encoding CSGP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding CSGP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode CSGP may be designed to contain signal sequences which direct secretion of CSGP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138), are available from the American Type Culture Collection (ATCC, Manassas, VA.) and may be chosen to ensure the correct modification and processing of the foreign protein.

In another embodiment of the invention, natural, modified, or recombinant nucleic acid sequences encoding CSGP may be ligated to a heterologous sequence resulting in translation of a fusion protein in any of the aforementioned host systems. For example, a chimeric CSGP protein containing a heterologous moiety that can be recognized by a commercially available antibody may facilitate the screening of peptide libraries for inhibitors of CSGP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the CSGP encoding sequence and the heterologous protein sequence, so that CSGP may be cleaved away from the heterologous moiety following purification. Methods for fusion protein expression and purification are discussed in Ausubel (1995, supra, ch 10). A variety of commercially available kits may also be used to facilitate expression and purification of fusion proteins.

In a further embodiment of the invention, synthesis of radiolabeled CSGP may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}$S-methionine.

Fragments of CSGP may be produced not only by recombinant production, but also by direct peptide synthesis using solid-phase techniques. (See, e.g., Creighton, supra, pp. 55–60.) Protein synthesis may be performed by manual techniques or by automation. Automated synthesis may be achieved, for example, using the ABI 431 A peptide synthesizer (Perkin-Elmer). Various fragments of CSGP may be synthesized separately and then combined to produce the full length molecule.

THERAPEUTICS

Chemical and structural similarity, e.g., in the context of sequences and motifs, exists between regions of CSGP-1 and XG and between regions of CSGP-2 and hPC-1. In addition, the expression of CSGP-1 is closely associated with vascular tissue, and the expression of CSGP-2 is closely associated with brain tissue. Therefore, CSGP appears to play a role in hematologic, karyotypic, and neuronal disorders. In the treatment of hematologic, karyotypic, and neuronal disorders associated with increased CSGP expression or activity, it is desirable to decrease the expression or activity of CSGP. In the treatment of the above conditions associated with decreased CSGP expression or activity, it is desirable to increase the expression or activity of CSGP.

Therefore, in one embodiment, CSGP or a fragment or derivative thereof may be administered to a subject to treat or prevent a disorder associated with decreased expression or activity of CSGP. Examples of such disorders include, but are not limited to, a hematologic disorder such as anemia including β-thalassemia, hemorrhage, thrombosis, embolism, lymphadenopathy, splenomegaly, phagocytic disorders, hematopoietic disorders, hemoglobin disorders including sickle cell anemia, bone marrow disorders, leukemia including chronic myelogenous leukemia and other myeloproliferative disorders, lymphoma including non-Hodgkin's lymphoma, Hodgkin's disease, complications related to blood transfusion, complications related to bone marrow transplantation, and clotting disorders including von Willebrand's disease and hemophilia; a karyotypic disorder associated with sex chromosome imbalance including Klinefelter syndrome and Turner syndrome; and a neuronal disorder such as akathesia, Alzheimer's disease, amnesia, amyotrophic lateral sclerosis, bipolar disorder, catatonia, cerebral neoplasms, dementia, depression, diabetic neuropathy, Down's syndrome, tardive dyskinesia, dystonias, epilepsy, Huntington's disease, peripheral neuropathy, multiple sclerosis, neurofibromatosis, Parkinson's disease, paranoid psychoses, postherpetic neuralgia, schizophrenia, and Tourette's disorder.

In another embodiment, a vector capable of expressing CSGP or a fragment or derivative thereof may be administered to a subject to treat or prevent a disorder associated with decreased expression or activity of CSGP including, but not limited to, those described above.

In a further embodiment, a pharmaceutical composition comprising a substantially purified CSGP in conjunction with a suitable pharmaceutical carrier may be administered to a subject to treat or prevent a disorder associated with decreased expression or activity of CSGP including, but not limited to, those provided above.

In still another embodiment, an agonist which modulates the activity of CSGP may be administered to a subject to treat or prevent a disorder associated with decreased expression or activity of CSGP including, but not limited to, those listed above.

In a further embodiment, an antagonist of CSGP may be administered to a subject to treat or prevent a disorder associated with increased expression or activity of CSGP. Examples of such disorders include, but are not limited to, those hematologic, karyotypic, and neuronal disorders described above. In one aspect, an antibody which specifically binds CSGP may be used directly as an antagonist or indirectly as a targeting or delivery mechanism for bringing a pharmaceutical agent to cells or tissue which express CSGP.

In an additional embodiment, a vector expressing the complement of the polynucleotide encoding CSGP may be administered to a subject to treat or prevent a disorder associated with increased expression or activity of CSGP including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of CSGP may be produced using methods which are generally known in the art. In particular, purified CSGP may be used to produce antibodies or to screen libraries of pharmaceutical agents to identify those which specifically bind CSGP. Antibodies to CSGP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with CSGP or with any fragment or oligopeptide thereof which has immunogenic properties. Depending on the host species, various adjuvants may be used to increase immunological response. Such adjuvants include, but are not limited to, Freund's , mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to CSGP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of CSGP amino acids may be fused with those of another protein, such as KLH, and antibodies to the chimeric molecule may be produced.

Monoclonal antibodies to CSGP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce CSGP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; Winter, G. et al. (1991) Nature 349:293–299.)

Antibody fragments which contain specific binding sites for CSGP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between CSGP and its specific antibody. A two-site, monoclonal-based immunoassay utilizing monoclonal antibodies reactive to two non-interfering CSGP epitopes is preferred, but a competitive binding assay may also be employed (Pound, supra).

Various methods such as Scatchard analysis in conjunction with radioimmunoassay techniques may be used to assess the affinity of antibodies for CSGP. Affinity is expressed as an association constant, $K_a$, which is defined as the molar concentration of CSGP-antibody complex divided by the molar concentrations of free antigen and free antibody under equilibrium conditions. The $K_a$ determined for a preparation of polyclonal antibodies, which are heterogeneous in their affinities for multiple CSGP epitopes, represents the average affinity, or avidity, of the antibodies for CSGP. The $K_a$ determined for a preparation of monoclonal antibodies, which are monospecific for a particular CSGP epitope, represents a true measure of affinity. High-affinity antibody preparations with $K_a$ ranging from about $10^9$ to $10^{12}$ L/mole are preferred for use in immunoassays in which the CSGP-antibody complex must withstand rigorous manipulations. Low-affinity antibody preparations with $K_a$ ranging from about $10^6$ to $10^7$ L/mole are preferred for use in immunopurification and similar procedures which ultimately require dissociation of CSGP, preferably in active form, from the antibody (Catty, D. (1988) *Antibodies, Volume I: A Practical Approach*, IRL Press, Washington, D.C.; Liddell, J. E. and Cryer, A. (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is preferred for use in procedures requiring precipitation of CSGP-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding CSGP, or any fragment or complement thereof, may be used for therapeutic purposes. In one aspect, the complement of the polynucleotide encoding CSGP may be used in situations in which it would be desirable to block the transcription of the mRNA. In particular, cells may be transformed with sequences complementary to polynucleotides encoding CSGP. Thus, complementary molecules or fragments may be used to modulate CSGP activity, or to achieve regulation of gene function. Such technology is now well known in the art, and sense or antisense oligonucleotides or larger fragments can be designed from various locations along the coding or control regions of sequences encoding CSGP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding CSGP. (See, e.g., Sambrook, supra; Ausubel, 1995, supra.)

Genes encoding CSGP can be turned off by transforming a cell or tissue with expression vectors which express high levels of a polynucleotide, or fragment thereof, encoding CSGP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding CSGP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding CSGP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding CSGP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of CSGP, antibodies to CSGP, and mimetics, agonists, antagonists, or inhibitors of CSGP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of CSGP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example CSGP or fragments thereof, antibodies of CSGP, and agonists, antagonists or inhibitors of CSGP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment.

Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind CSGP may be used for the diagnosis of disorders characterized by expression of CSGP, or in assays to monitor patients being treated with CSGP or agonists, antagonists, or inhibitors of CSGP. Antibodies useful for diagnostic purposes may be prepared in the same manner as described above for therapeutics. Diagnostic assays for CSGP include methods which utilize the antibody and a label to detect CSGP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring CSGP, including ELISAs, RIAs, and FACS, are known in the art and provide a basis for diagnosing altered or abnormal levels of CSGP expression. Normal or standard values for CSGP expression are established by combining body fluids or cell extracts taken from normal mammalian subjects, preferably human, with antibody to CSGP under conditions suitable for complex formation. The amount of standard complex formation may be quantitated by various methods, preferably by photometric means. Quantities of CSGP expressed in subject samples from biopsied tissues are compared with the standard values. Deviation between standard and subject values establishes the parameters for diagnosing disease.

In another embodiment of the invention, the polynucleotides encoding CSGP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of CSGP may be correlated with disease. The diagnostic assay may be used to determine absence, presence, and excess expression of CSGP, and to monitor regulation of CSGP levels during therapeutic intervention.

In one aspect, hybridization with PCR probes which are capable of detecting polynucleotide sequences, including genomic sequences, encoding CSGP or closely related molecules may be used to identify nucleic acid sequences which encode CSGP. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding CSGP, allelic variants, or related sequences.

Probes may also be used for the detection of related sequences, and should preferably have at least 50% sequence identity to any of the CSGP encoding sequences. The hybridization probes of the subject invention may be DNA or RNA and may be derived from the sequence of SEQ ID NO:3 or SEQ ID NO:4 or from genomic sequences including promoters, enhancers, and introns of the CSGP gene.

Means for producing specific hybridization probes for DNAs encoding CSGP include the cloning of polynucleotide sequences encoding CSGP or CSGP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding CSGP may be used for the diagnosis of disorders associated with expression of CSGP. Examples of such disorders include, but are not limited to, a hematologic disorder such as anemia including β-thalassemia, hemorrhage, thrombosis, embolism, lymphadenopathy, splenomegaly, phagocytic disorders, hematopoietic disorders, hemoglobin disorders including sickle cell anemia, bone marrow disorders, leukemia including chronic myelogenous leukemia and other myeloproliferative disorders, lymphoma including non-Hodgkin's lymphoma, Hodgkin's disease, complications related to blood transfusion, complications related to bone marrow transplantation, and clotting disorders including von Willebrand's disease and hemophilia; a karyotypic disorder associated with sex chromosome imbalance including Klinefelter syndrome and Turner syndrome; and a neuronal disorder such as akathesia, Alzheimer's disease, amnesia, amyotrophic lateral sclerosis, bipolar disorder, catatonia, cerebral neoplasms, dementia, depression, diabetic neuropathy, Down's syndrome, tardive dyskinesia, dystonias, epilepsy, Huntington's disease, peripheral neuropathy, multiple sclerosis, neurofibromatosis, Parkinson's disease, paranoid psychoses, postherpetic neuralgia, schizophrenia, and Tourette's disorder. The polynucleotide sequences encoding CSGP may be used in Southern or northern analysis, dot blot, or other membrane-based technologies; in PCR technologies; in dipstick, pin, and multiformat ELISA-like assays; and in microarrays utilizing fluids or tissues from patients to detect altered CSGP expression. Such qualitative or quantitative methods are well known in the art.

In a particular aspect, the nucleotide sequences encoding CSGP may be useful in assays that detect the presence of associated disorders, particularly those mentioned above. The nucleotide sequences encoding CSGP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding CSGP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of CSGP, a normal or standard profile for expression is established. This may be accomplished by combining body fluids or cell extracts taken from normal subjects, either animal or human, with a sequence, or a fragment thereof, encoding CSGP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding CSGP may involve the use of PCR. These oligomers may be chemically synthesized, generated enzymatically, or produced in vitro. Oligomers will preferably contain a fragment of a polynucleotide encoding CSGP, or a fragment of a polynucleotide complementary to the polynucleotide encoding CSGP, and will be employed under optimized conditions for identification of a specific gene or condition. Oligomers may also be employed under less stringent conditions for detection or quantitation of closely related DNA or RNA sequences.

Methods which may also be used to quantitate the expression of CSGP include radiolabeling or biotinylating nucleotides, coamplification of a control nucleic acid, and interpolating results from standard curves. (See, e.g., Melby, P. C. et al. (1993) J. Immunol. Methods 159:235–244; Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding CSGP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat. Genet. 15:345–355; Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, supra, pp. 965–968.) Examples of genetic map data can be found in various scientific journals or at the Online Mendelian Inheritance in Man (OMIM) site. Correlation between the location of the gene encoding CSGP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, CSGP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between CSGP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with CSGP, or fragments thereof, and washed. Bound CSGP is then detected by methods well known in the art. Purified CSGP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding CSGP specifically compete with a test compound for binding CSGP. In this manner, antibodies can be used to detect the presence of any peptide which shares one or more antigenic determinants with CSGP.

In additional embodiments, the nucleotide sequences which encode CSGP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. Construction of cDNA Libraries

The BRSTNOT05 cDNA library was constructed using RNA isolated from breast tissue removed from a 58-year-old Caucasian female during a unilateral extended simple mastectomy. Pathology for the associated tumor tissue indicated multicentric invasive grade 4 lobular carcinoma. Patient history included skin cancer, rheumatic heart disease, osteoarthritis, and tuberculosis. Family history included cerebrovascular and cardiovascular disease, breast and prostate cancer, and type I diabetes.

The PONSAZT01 cDNA library was constructed using RNA isolated from diseased pons tissue removed from the brain of a 74-year-old Caucasian male who died from Alzheimer's disease.

Frozen tissue from each of the above sources was homogenized and lysed in guanidinium isothiocyanate solution using a Polytron PT-3000 homogenizer (Brinkmann Instruments, Westbury N.Y.). The lysate was centrifuged over a CsCl cushion to isolate RNA. The RNA was extracted with acid phenol, precipitated with sodium acetate and ethanol, resuspended in RNase-free water, and treated with DNase. The RNA was re-extracted with acid phenol and reprecipitated as described above. Poly(A+) RNA was isolated using the OLIGOTEX mRNA purification kit (QIAGEN, Chatsworth Calif.).

Poly(A+) RNA was used for cDNA synthesis and construction of the cDNA library according to the recommended protocols in the SUPERSCRIPT plasmid system (Life Technologies). The cDNAs were fractionated on a SEPHAROSE CL4B column (Amersham Pharmacia Biotech), and those cDNAs exceeding 400 bp were used for library construction. cDNAs used to construct BRSTNOT05 were ligated into PSPORT1 (Life Technologies), and cDNAs used to construct PONSAZT01 were ligated into pINCY (Incyte Pharmaceuticals, Palo Alto Calif.). Recombinant plasmids were transformed into DH5α competent cells (Life Technologies).

II. Isolation of cDNA Clones

For each of the above cDNA libraries, plasmid DNA was released from host cells and purified using the R.E.A.L. PREP 96 plasmid kit (QIAGEN). The recommended protocol was employed except for the following changes:1) the bacteria were cultured in 1 ml of sterile Terrific Broth (Life Technologies) with carbenicillin at 25 mg/l and glycerol at 0.4%; 2) after the cultures were incubated for 19 hours, the cells were lysed with 0.3 ml of lysis buffer; and 3) following isopropanol precipitation, the plasmid DNA pellets were each resuspended in 0.1 ml of distilled water. The DNA samples were stored at 4° C.

III. Sequencing and Analysis

The cDNAs were prepared for sequencing using the ABI CATALYST 800 (Perkin-Elmer) or the HYDRA microdispenser (Robbins Scientific) or MICROLAB 2200 (Hamilton) systems in combination with the PTC-200 thermal cyclers (MJ Research). The cDNAs were sequenced using the ABI PRISM 373 or 377 sequencing systems (Perkin-Elmer) and standard ABI protocols, base calling software, and kits. In one alternative, cDNAs were sequenced using the MEGABACE 1000 DNA sequencing system (Molecular Dynamics). In another alternative, the cDNAs were amplified and sequenced using the ABI PRISM BIGDYE Terminator cycle sequencing ready reaction kit (Perkin-Elmer). In yet another alternative, cDNAs were sequenced using solutions and dyes from Amersham Pharmacia Biotech. Reading frames for the ESTs were determined using standard methods (reviewed in Ausubel, 1997, supra, unit 7.7). Some of the cDNA sequences were selected for extension using the techniques disclosed in Example V.

The polynucleotide sequences derived from cDNA, extension, and shotgun sequencing were assembled and analyzed using a combination of software programs which utilize algorithms well known to those skilled in the art. Table 1 summarizes the software programs, descriptions, references, and threshold parameters used. The first column of Table 1 shows the tools, programs, and algorithms used, the second column provides a brief description thereof, the third column presents the references which are incorporated by reference herein, and the fourth column presents, where applicable, the scores, probability values, and other parameters used to evaluate the strength of a match between two sequences (the higher the probability the greater the homology). Sequences were analyzed using MACDNASIS PRO software (Hitachi Software Engineering, South San Francisco Calif.) and LASERGENE software (DNASTAR).

The polynucleotide sequences were validated by removing vector, linker, and polyA sequences and by masking ambiguous bases, using algorithms and programs based on BLAST, dynamic programing, and dinucleotide nearest neighbor analysis. The sequences were then queried against a selection of public databases such as GenBank primate, rodent, mammalian, vertebrate, and eukaryote databases, and BLOCKS to acquire annotation, using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA. The full length polynucleotide sequences were translated to derive the corresponding full length amino acid sequences, and these full length sequences were subsequently analyzed by querying against databases such as the GenBank databases (described above), SwissProt, BLOCKS, PRINTS, Prosite, and Hidden Markov Model (HMM)-based protein family databases such as PFAM. HMM is a probalistic approach which analyzes consensus primary structures of gene families. (See, e.g., Eddy, S. R. (1996) Cur. Opin. Str. Biol. 6:361–365.)

The programs described above for the assembly and analysis of full length polynucleotide and amino acid sequences were also used to identify polynucleotide sequence fragments from SEQ ID NO:3 and SEQ ID NO:4. Fragments from about 20 to about 4000 nucleotides which are useful in hybridization and amplification technologies were described in The Invention section above.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel, 1995, supra, ch. 4 and 16.)

Analogous computer techniques applying BLAST were used to search for identical or related molecules in nucleotide databases such as GenBank or LIFESEQ database (Incyte Pharmaceuticals). This analysis is much faster than multiple membrane-based hybridizations. In addition, the sensitivity of the computer search can be modified to determine whether any particular match is categorized as exact or similar. The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of northern analyses are reported as a percentage distribution of libraries in which the transcript encoding CSGP occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease/condition categories included cancer, inflammation/trauma, cell proliferation, neurological, and pooled. For each category, the number of libraries expressing the sequence of interest was counted and divided by the total number of libraries across all categories. Percentage values of tissue-specific and disease- or condition-specific expression are reported in The Invention.

V. Extension of CSGP Encoding Polynucleotides

The full length nucleic acid sequences of SEQ ID NO:3 and SEQ ID NO:4 were produced by extension of an appropriate fragment of the full length molecule using oligonucleotide primers designed from this fragment. One primer was synthesized to initiate 5' extension of the known fragment, and the other primer, to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1:94° C., 3 min; Step 2:94° C., 15 sec; Step 3:60° C., 1 min; Step 4:68° C., 2 min; Step 5: Steps 2, 3, and 4 repeated 20 times; Step 6:68° C., 5 min; Step 7: storage at 4° C. In the alternative, the parameters for primer pair T7 and SK+ were as follows: Step 1:94° C., 3 min; Step 2:94° C., 15 sec; Step 3:57° C., 1 min; Step 4:68° C., 2 min; Step 5: Steps 2, 3, and 4 repeated 20 times; Step 6:68° C., 5 min; Step 7: storage at 4° C.

The concentration of DNA in each well was determined by dispensing 100 µl PICOGREEN quantitation reagent (0.25% (v/v) PICOGREEN; Molecular Probes, Eugene Oreg.) dissolved in 1× TE and 0.5 µl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 µl to 10 µl aliquot of the reaction mixture was analyzed by electrophoresis on a 1% agarose mini-gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent E. coli cells. Transformed cells were selected on antibiotic-containing media, individual colonies were picked and cultured overnight at 37° C. in 384-well plates in LB/2× carb liquid media.

The cells were lysed, and DNA was amplified by PCR using Taq DNA polymerase (Amersham Pharmacia Biotech) and Pfu DNA polymerase (Stratagene) with the following parameters: Step 1:94° C., 3 min; Step 2:94° C., 15 sec; Step 3:60° C., 1 min; Step 4:72° C., 2 min; Step 5: steps 2, 3, and 4 repeated 29 times; Step 6:72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Perkin-Elmer).

In like manner, the nucleotide sequences of SEQ ID NO:3 and SEQ ID NO:4 are used to obtain 5' regulatory sequences using the procedure above, oligonucleotides designed for such extension, and an appropriate genomic library.

VI. Labeling and Use of Individual Hybridization Probes

Hybridization probes derived from SEQ ID NO:3 and SEQ ID NO:4 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 $\mu$Ci of [$\gamma$-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xbal, or Pvu II (DuPont NEN).

The DNA from each digest is fractionated on a 0.7% agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT-AR film (Eastman Kodak, Rochester N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the CSGP-encoding sequences, or any parts thereof, are used to detect, decrease, or inhibit expression of naturally occurring CSGP. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of CSGP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the CSGP-encoding transcript.

IX. Expression of CSGP

Expression and purification of CSGP is achieved using bacterial or virus-based expression systems. For expression of CSGP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express CSGP upon induction with isopropyl beta-D-thiogalactopyranoside (IPTG). Expression of CSGP in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding CSGP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, CSGP is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from CSGP at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch 10 and 16). Purified CSGP obtained by these methods can be used directly in the following activity assay.

X. Demonstration of CSGP Activity

An assay for CSGP activity measures the expression of CSGP on the cell surface. cDNA encoding CSGP is transfected into a cell line that does not express endogenous CSGP. Cell surface proteins of transfectants are labeled with biotin (de la Fuente, M. A. et al. (1997) Blood 90:2398–2405). Immunoprecipitations are performed using CSGP-specific antibodies, and immunoprecipitated samples are analyzed using SDS-PAGE and immunoblotting techniques. The ratio of labeled immunoprecipitant to unlabeled immunoprecipitant is proportional to the amount of CSGP expressed on the cell surface.

XI. Functional Assays

CSGP function is assessed by expressing the sequences encoding CSGP at physiologically elevated levels in mammalian cell culture systems. cDNA is subcloned into a mammalian expression vector containing a strong promoter that drives high levels of cDNA expression. Vectors of choice include pCMV SPORT (Life Technologies) and pCR3.1 (Invitrogen, Carlsbad Calif.), both of which contain the cytomegalovirus promoter. 5–10 μg of recombinant vector are transiently transfected into a human cell line, preferably of endothelial or hematopoietic origin, using either liposome formulations or electroporation. 1–2 μg of an additional plasmid containing sequences encoding a marker protein are cotransfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) Flow Cytometry, Oxford, New York N.Y.

The influence of CSGP on gene expression can be assessed using highly purified populations of cells transfected with sequences encoding CSGP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding CSGP and other genes of interest can be analyzed by northern analysis or microarray techniques.

XII. Production of CSGP Specific Antibodies

CSGP substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the CSGP amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides 15 residues in length are synthesized using an ABI 431A peptide synthesizer (Perkin-Elmer) using fmoc-chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring CSGP Using Specific Antibodies

Naturally occurring or recombinant CSGP is substantially purified by immunoaffinity chromatography using antibodies specific for CSGP. An immunoaffinity column is constructed by covalently coupling anti-CSGP antibody to an activated chromatographic resin, such as CNBr-activated SEPHAROSE (Amersham Pharmacia Biotech). After the coupling, the resin is blocked and washed according to the manufacturer's instructions.

Media containing CSGP are passed over the immunoaffinity column, and the column is washed under conditions that allow the preferential absorbance of CSGP (e.g., high ionic strength buffers in the presence of detergent). The column is eluted under conditions that disrupt antibody/CSGP binding (e.g., a buffer of pH 2 to pH 3, or a high concentration of a chaotrope, such as urea or thiocyanate ion), and CSGP is collected.

XIV. Identification of Molecules Which Interact with CSGP

CSGP, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled CSGP, washed, and any wells with labeled CSGP complex are assayed. Data obtained using different concentrations of CSGP are used to calculate values for the number, affinity, and association of CSGP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City, CA. | |
| ABI/PARACEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch < 50% |
| ABI AutoAssembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215:403–410; Altschul, S. F. et al. (1997) Nucleic Acids Res. 25: 3389–3402. | ESTs: Probability value = 1.0E-8 or less<br>Full Length sequences: Probability value = 1.0E-10 or less |
| FASTA | A Pearson and Lipman algorithm that searches for similarity between a query sequence and a group of sequences of the same type. FASTA comprises at least five functions: fasta, tfasta, fastx, tfastx, and ssearch. | Pearson, W. R. and D. J. Lipman (1988) Proc. Natl. Acad. Sci. 85:2444–2448; Pearson, W. R. (1990) Methods Enzymol. 183:63–98; and Smith, T. F. and M. S. Waterman (1981) Adv. Appl. Math. 2:482–489. | ESTs: fasta E value = 1.06E-6 Assembled ESTs: fasta Identity = 95% or greater and Match length = 200 bases or greater, fastx E value-10E-8 or less<br>Full Length sequences: fastx score = 100 or greater |
| BLIMPS | A Blocks IMProvedSearcher that matches a sequence against those in BLOCKS and PRINTS databases to search for gene families, sequence homology, and structural fingerprint regions. | Henikoff, S and J. G. Henikoff, Nucl. Acid Res., 19:6565–72, 1991. J. G. Henikoff and S. Henikoff(1996) Methods Enzymol. 266:88–105; and Attwood, T. K. et al. (1997) J. Chem. Inf. Comput. Sci. 37:417–424. | Score = 1000 or greater; Ratio of Score/Strength = 0.75 or larger, and Probability value = 1.0E-3 or less |
| PFAM | A Hidden Markov Models-based application useful for protein family search. | Krogh, A. et al. (1994) J. Mol. Biol., 235:1501–1531; Sonnhammer, E.L.L. et al. (1988) Nucleic Acids Res. 26:320–322. | Score = 10–50 bits, depending on individual protein families |
| ProfileScan | An algorithm that searches for structural and sequence motifs in protein sequences that match sequence patterns defined in Prosite. | Gribskov, M. et al. (1988) CABIOS 4:61–66; Gribskov, et al. (1989) Methods Enzymol. 183:146–159; Bairoch, A. et al. (1997) Nucleic Acids Res. 25:217–221. | Score = 4.0 or greater |
| Phred | A base-calling algorithm that examines automated sequencer traces with high sensitivity and probability. | Ewing, B. et al. (1998) Genome Res. 8:175–185; Bwing, B. and P. Green (1998) Genome Res. 8:186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2:482–489; Smith, T. F. and M. S. Waterman (1981) J. Mol. Biol. 147:195–197; and Green, P., University of washington, Seattle, WA. | Score = 120 or greater; Match length = 56 or greater |
| Consed | A graphical tool for viewing and editing Phrap assemblies | Gordon, D. et al. (1998) Genome Res. 8:195–202. | |
| SPScan | A weight matrix analysis program that scans protein sequences for the presence of secretory signal peptides. | Nielson, H. et al. (1997) Protein Engineering 10:1–6; Claverie, J. M. and S. Audic (1997) CABIOS 12:431–439. | Score = 5 or greater |
| Motifs | A program that searches amino acid sequences for patterns that matched those defined in Prosite. | Bairoch et al. supra; Wisconsin Package Program Manual, version 9, page M51–59, Genetics Computer Group, Madison, WI. | |

What is claimed is:

1. An isolated and purified polynucleotide encoding CSGP-1 comprising the amino acid sequence of SEQ ID NO:1 or CSGP-2 comprising the amino acid sequence of SEQ ID NO:2.

2. An isolated and purified polynucleotide comprising a sequence which is completely complementary to the polynucleotide of claim 1.

3. A method for detecting a polynucleotide, the method comprising the steps of:
   (a) hybridizing the polynucleotide of claim 2 to at least one nucleic acid in a sample, thereby forming a hybridization complex whereby hybridization occurs at 42° C. in 250 mM NaCl, 25 mM trisodium citrate, 1% SDS, 50% formamide, and 200 µg/ml ssDNA and wash occurs at 68° C. in 15 mM NaCl, 1.5 mM trisodium citrate and 0.1% SDS; and
   (b) detecting the hybridization complex, wherein the presence of the hybridization complex correlates with the presence of the polynucleotide in the sample.

4. The method of claim 3 further comprising amplifying the polynucleotide prior to hybridization.

5. An isolated and purified polynucleotide comprising a polynucleotide sequence selected from the group consisting of SEQ ID NO:3 and SEQ ID NO:4.

6. An isolated and purified polynucleotide comprising a sequence which is completely complementary to the polynucleotide of claim 5.

7. An expression vector comprising the polynucleotide of claim 1.

8. A host cell comprising the expression vector of claim 7.

9. A method for producing a polypeptide, the method comprising the steps of:
   a) culturing the host cell of claim 8 under conditions suitable for the expression of the polypeptide; and
   b) recovering the polypeptide from the host cell culture.

* * * * *

SEQUENCE LISTING

<160> NUMBER OF SEQ ID NOS: 6

<210> SEQ ID NO 1
<211> LENGTH: 195
<212> TYPE: PRT
<213> ORGANISM: Homo sapiens
<220> FEATURE: -
<223> OTHER INFORMATION: 2297891

<400> SEQUENCE: 1

Met Glu Ser Trp Trp Gly Leu Pro Cys Leu Ala Phe Leu Cys Phe
 1               5                  10                  15

Leu Met His Ala Arg Gly Gln Arg Asp Phe Asp Leu Ala Asp Ala
                20                  25                  30

Leu Asp Asp Pro Glu Pro Thr Lys Lys Pro Asn Ser Asp Ile Tyr
                35                  40                  45

Pro Lys Pro Lys Pro Pro Tyr Tyr Pro Gln Pro Glu Asn Pro Asp
                50                  55                  60

Ser Gly Gly Asn Ile Tyr Pro Arg Pro Lys Pro Arg Pro Gln Pro
                65                  70                  75

Gln Pro Gly Asn Ser Gly Asn Ser Gly Gly Tyr Phe Asn Asp Val
                80                  85                  90

Asp Arg Asp Asp Gly Arg Tyr Pro Pro Arg Pro Arg Pro Arg Pro
                95                  100                 105

Pro Ala Gly Gly Gly Gly Gly Tyr Ser Ser Tyr Gly Asn Ser
                110                 115                 120

Asp Asn Thr His Gly Arg Gly Gly Tyr Arg Pro Asn Ser Arg Tyr
                125                 130                 135

Gly Asn Thr Tyr Gly Gly Asp His His Ser Thr Tyr Gly Asn Pro
                140                 145                 150

Glu Gly Asn Met Val Ala Lys Ile Val Ser Pro Ile Val Ser Val
                155                 160                 165

Val Val Val Thr Leu Leu Gly Ala Ala Ala Ser Tyr Phe Lys Leu
                170                 175                 180

Asn Asn Arg Arg Asn Cys Phe Arg Thr His Glu Pro Glu Asn Val
                185                 190                 195

<210> SEQ ID NO 2
<211> LENGTH: 438
<212> TYPE: PRT
<213> ORGANISM: Homo sapiens
<220> FEATURE: -
<223> OTHER INFORMATION: 2705267

<400> SEQUENCE: 2

Met Ala Val Lys Leu Gly Thr Leu Leu Leu Ala Leu Ala Leu Gly
 1               5                  10                  15

Leu Ala Gln Pro Ala Ser Ala Arg Arg Lys Leu Leu Val Phe Leu
                20                  25                  30

Leu Asp Gly Phe Arg Ser Asp Tyr Ile Ser Asp Glu Ala Leu Glu
                35                  40                  45

Ser Leu Pro Gly Phe Lys Glu Ile Val Ser Arg Gly Val Lys Val
                50                  55                  60

Asp Tyr Leu Thr Pro Asp Phe Pro Ser Leu Ser Tyr Pro Asn Tyr
                65                  70                  75

Tyr Thr Leu Met Thr Gly Arg His Cys Glu Val His Gln Met Ile

```
                    80                  85                  90
Gly Asn Tyr Met Trp Asp Pro Thr Thr Asn Lys Ser Phe Asp Ile
                    95                 100                 105
Gly Val Asn Lys Asp Ser Leu Met Pro Leu Trp Asn Gly Ser
                110                 115                 120
Glu Pro Leu Trp Val Thr Leu Thr Lys Ala Lys Arg Lys Val Tyr
                125                 130                 135
Met Tyr Tyr Trp Pro Gly Cys Glu Val Glu Ile Leu Gly Val Arg
                140                 145                 150
Pro Thr Tyr Cys Leu Glu Tyr Lys Asn Val Pro Thr Asp Ile Asn
                155                 160                 165
Phe Ala Asn Ala Val Ser Asp Ala Leu Asp Ser Phe Lys Ser Gly
                170                 175                 180
Arg Ala Asp Leu Ala Ala Ile Tyr His Glu Arg Ile Asp Val Glu
                185                 190                 195
Gly His His Tyr Gly Pro Ala Ser Pro Gln Arg Lys Asp Ala Leu
                200                 205                 210
Lys Ala Val Asp Thr Val Leu Lys Tyr Met Thr Lys Trp Ile Gln
                215                 220                 225
Glu Arg Gly Leu Gln Asp Arg Leu Asn Val Ile Ile Phe Ser Asp
                230                 235                 240
His Gly Met Thr Asp Ile Phe Trp Met Asp Lys Val Ile Glu Leu
                245                 250                 255
Asn Lys Tyr Ile Ser Leu Asn Asp Leu Gln Gln Val Lys Asp Arg
                260                 265                 270
Gly Pro Val Val Ser Leu Trp Pro Ala Pro Gly Lys His Ser Glu
                275                 280                 285
Ile Tyr Asn Lys Leu Ser Thr Val Glu His Met Thr Val Tyr Glu
                290                 295                 300
Lys Glu Ala Ile Pro Ser Arg Phe Tyr Lys Lys Gly Lys Phe
                305                 310                 315
Val Ser Pro Leu Thr Leu Val Ala Asp Glu Gly Trp Phe Ile Thr
                320                 325                 330
Glu Asn Arg Glu Met Leu Pro Phe Trp Met Asn Ser Thr Gly Arg
                335                 340                 345
Arg Glu Gly Trp Gln Arg Gly Trp His Gly Tyr Asp Asn Glu Leu
                350                 355                 360
Met Asp Met Arg Gly Ile Phe Leu Thr Leu Gly Pro Gly Arg Arg
                365                 370                 375
Gly Asn Asp Gln Met Leu Ser Asp Pro Ile Pro Lys Glu Val Ser
                380                 385                 390
Leu Arg Gly Pro Thr Gly Ala Arg Arg Gly Cys Arg Asp Phe Leu
                395                 400                 405
Thr Asp Pro Leu Tyr Glu Pro Ser Arg Ala Asn Pro Ala Gly Leu
                410                 415                 420
His Glu Thr Ser Phe Ala Gly Phe Leu Ser Asn Ala Ser Trp Val
                425                 430                 435
Trp Gln Met

<210> SEQ ID NO 3
<211> LENGTH: 935
<212> TYPE: DNA
<213> ORGANISM: Homo sapiens
<220> FEATURE: -
```

<223> OTHER INFORMATION: 2297891

<400> SEQUENCE: 3

| | | | | | | |
|---|---|---|---|---|---|---|
| tgcagattgg | ttggggcagc | ccggggaggc | tggctccgac | acacgactga | gtgtgcctac | 60 |
| actggtccca | caggttttca | gctgtggagt | ttgggatctg | agcttggagc | ccatttgttt | 120 |
| ctggcagttc | cgctcatatt | ttccacttga | agacatcgcc | tcccttcctt | ccaagctggg | 180 |
| agaccagaag | tcaacaacag | gagggtggag | aggccgggtc | tcacaatccg | cttggctggg | 240 |
| gagtccactg | aggttcttgc | atcctgaagc | aaaccatgga | gagctggtgg | ggacttccct | 300 |
| gtcttgcgtt | cctgtgtttt | ctaatgcacg | cccgaggtca | aagagacttt | gattggcag | 360 |
| atgcccttga | tgaccctgaa | cccaccaaga | agccaaactc | agatatctac | ccaaagccaa | 420 |
| aaccacctta | ctacccacag | cccgagaatc | ccgacagcgg | tggaaatatc | tacccaaggc | 480 |
| caaagccacg | ccctcaaccc | cagcctggca | attccggcaa | cagtggaggt | tacttcaatg | 540 |
| atgtggaccg | tgatgacgga | cgctacccgc | ccaggcccag | gccacggccg | cctgcaggag | 600 |
| gtggcggcgg | tggctactcc | agttatggca | actccgacaa | cacgcacgga | agaggggct | 660 |
| atagacccaa | ctctcgttat | ggaaatactt | atggtggaga | tcaccattca | acgtatggca | 720 |
| atccagaagg | caatatggta | gcaaaaatcg | tgtctcccat | cgtatccgtg | gtggtggtga | 780 |
| cactgctggg | agcagcagcc | agttatttca | aactaaacaa | taggagaaat | tgtttcagga | 840 |
| cccatgaacc | agaaaatgtc | tgaagatgtt | aagatcccct | gattactttg | ggaaaaacaa | 900 |
| ctaaaacaag | aaccgtgttt | atcaaaaaaa | aaaaa | | | 935 |

<210> SEQ ID NO 4
<211> LENGTH: 1438
<212> TYPE: DNA
<213> ORGANISM: Homo sapiens
<220> FEATURE: -
<223> OTHER INFORMATION: 2705267

<400> SEQUENCE: 4

| | | | | | | |
|---|---|---|---|---|---|---|
| gagagaatag | ctacagattc | tccatcctca | gtctttgcaa | ggcgacagct | gtgccagccg | 60 |
| ggctctggca | ggctcctggc | agcatggcag | tgaagcttgg | gaccctcctg | ctggcccttg | 120 |
| ccctgggcct | ggcccagcca | gcctctgccc | gccggaagct | gctggtgttt | ctgctggatg | 180 |
| gttttcgctc | agactacatc | agtgatgagg | cgctggagtc | attgcctggt | tcaaagaga | 240 |
| ttgtgagcag | gggagtaaaa | gtggattact | tgactccaga | cttccctagt | ctctcgtatc | 300 |
| ccaattatta | taccctaatg | actggccgcc | attgtgaagt | ccatcagatg | atcgggaact | 360 |
| acatgtggga | ccccaccacc | aacaagtcct | ttgacattgg | cgtcaacaaa | gacagcctaa | 420 |
| tgcctctctg | gtggaatgga | tcagaacctc | tgtgggtcac | tctgaccaag | gccaaaagga | 480 |
| aggtctacat | gtactactgg | ccaggctgtg | aggttgagat | tctgggtgtc | agacccacct | 540 |
| actgcctaga | atataaaaat | gtcccaacgg | atatcaattt | tgccaatgca | gtcagcgatg | 600 |
| ctcttgactc | cttcaagagt | ggccgggccg | acctggcagc | catataccat | gagcgcattg | 660 |
| acgtggaagg | ccaccactac | gggcctgcat | ctccgcagag | gaaagatgcc | ctcaaggctg | 720 |
| tagacactgt | cctgaagtac | atgaccaagt | ggatccagga | gcggggcctg | caggaccgcc | 780 |
| tgaacgtcat | tattttctcg | gatcacggaa | tgaccgacat | tttctggatg | gacaaagtga | 840 |
| ttgagctgaa | taagtacatc | agcctgaatt | acctgcagca | agtgaaggac | cgcgggcctg | 900 |
| ttgtgagcct | ttgccggcc | cctgggaaac | actctgagat | atataacaaa | ctgagcacag | 960 |
| tggaacacat | gactgtctac | gagaaagaag | ccatcccaag | caggttctat | tacaagaaag | 1020 |

```
gaaagtttgt ctctcctttg actttagtgg ctgatgaagg ctggttcata actgagaatc    1080
gagagatgct tccgttttgg atgaacagca ccggcaggcg ggaaggttgg cagcgtggat    1140
ggcacggcta cgacaacgag ctcatggaca tgcggggcat cttcctgact ctcggacctg    1200
gtaggcgagg aaatgaccag atgctctcag accccattcc caaggaagtg tctctaaggg    1260
gccctacggg tgccaggaga ggctgcaggg atttcctcac agaccctctt tatgagccaa    1320
gcagagcaaa cccagccggt ctccatgaaa catcttttgc tggcttcctt tcaaatgctt    1380
cttgggtttg gcaaatgtag ccaaatactg tgccgtgtaa attttaaatc ctgcagca      1438
```

<210> SEQ ID NO 5
<211> LENGTH: 180
<212> TYPE: PRT
<213> ORGANISM: Homo sapiens
<220> FEATURE: -
<223> OTHER INFORMATION: g2499136

<400> SEQUENCE: 5

```
Met Glu Ser Trp Trp Gly Leu Pro Cys Leu Ala Phe Leu Cys Phe
 1               5                  10                  15

Leu Met His Ala Arg Gly Gln Arg Asp Phe Asp Leu Ala Asp Ala
                20                  25                  30

Leu Asp Asp Pro Glu Pro Thr Lys Lys Pro Asn Ser Asp Ile Tyr
                35                  40                  45

Pro Lys Pro Lys Pro Pro Tyr Tyr Pro Gln Pro Glu Asn Pro Asp
                50                  55                  60

Ser Gly Gly Asn Ile Tyr Pro Arg Pro Lys Pro Arg Pro Gln Pro
                65                  70                  75

Gln Pro Gly Asn Ser Gly Asn Ser Gly Gly Tyr Phe Asn Asp Val
                80                  85                  90

Asp Arg Asp Asp Gly Arg Tyr Pro Pro Arg Pro Arg Pro Arg Pro
                95                 100                 105

Pro Ala Gly Gly Gly Gly Gly Tyr Ser Ser Tyr Gly Asn Ser
               110                 115                 120

Asp Asn Thr His Gly Gly Asp His His Ser Thr Tyr Gly Asn Pro
               125                 130                 135

Glu Gly Asn Met Val Ala Lys Ile Val Ser Pro Ile Val Ser Val
               140                 145                 150

Val Val Val Thr Leu Leu Gly Ala Ala Ala Ser Tyr Phe Lys Leu
               155                 160                 165

Asn Asn Arg Arg Asn Cys Phe Arg Thr His Glu Pro Glu Asn Val
               170                 175                 180
```

<210> SEQ ID NO 6
<211> LENGTH: 873
<212> TYPE: PRT
<213> ORGANISM: Homo sapiens
<220> FEATURE: -
<223> OTHER INFORMATION: g189650

<400> SEQUENCE: 6

```
Met Asp Val Gly Glu Glu Pro Leu Glu Lys Ala Ala Arg Ala Arg
 1               5                  10                  15

Thr Ala Lys Asp Pro Asn Thr Tyr Lys Val Leu Ser Leu Val Leu
                20                  25                  30

Ser Val Cys Val Leu Thr Thr Ile Leu Gly Cys Ile Phe Gly Leu
                35                  40                  45
```

```
Lys Pro Ser Cys Ala Lys Glu Val Lys Ser Cys Lys Gly Arg Cys
                 50                  55                  60

Phe Glu Arg Thr Phe Gly Asn Cys Arg Cys Asp Ala Ala Cys Val
                 65                  70                  75

Glu Leu Gly Asn Cys Cys Leu Asp Tyr Gln Glu Thr Cys Ile Glu
                 80                  85                  90

Pro Glu His Ile Trp Thr Cys Asn Lys Phe Arg Cys Gly Glu Lys
                 95                 100                 105

Arg Leu Thr Arg Ser Leu Cys Ala Cys Ser Asp Asp Cys Lys Asp
                110                 115                 120

Lys Gly Asp Cys Cys Ile Asn Tyr Ser Ser Val Cys Gln Gly Glu
                125                 130                 135

Lys Ser Trp Val Glu Glu Pro Cys Glu Ser Ile Asn Glu Pro Gln
                140                 145                 150

Cys Pro Ala Gly Phe Glu Thr Pro Pro Thr Leu Leu Phe Ser Leu
                155                 160                 165

Asp Gly Phe Arg Ala Glu Tyr Leu His Thr Trp Gly Gly Leu Leu
                170                 175                 180

Pro Val Ile Ser Lys Leu Lys Lys Cys Gly Thr Tyr Thr Lys Asn
                185                 190                 195

Met Arg Pro Val Tyr Pro Thr Lys Thr Phe Pro Asn His Tyr Ser
                200                 205                 210

Ile Val Thr Gly Leu Tyr Pro Glu Ser His Gly Ile Ile Asp Asn
                215                 220                 225

Lys Met Tyr Asp Pro Lys Met Asn Ala Ser Phe Ser Leu Lys Ser
                230                 235                 240

Lys Glu Lys Phe Asn Pro Glu Trp Tyr Lys Gly Glu Pro Ile Trp
                245                 250                 255

Val Thr Ala Lys Tyr Gln Gly Leu Lys Ser Gly Thr Phe Phe Trp
                260                 265                 270

Pro Gly Ser Asp Val Glu Ile Asn Gly Ile Phe Pro Asp Ile Tyr
                275                 280                 285

Lys Met Tyr Asn Gly Ser Val Pro Phe Glu Glu Arg Ile Leu Ala
                290                 295                 300

Val Leu Gln Trp Leu Gln Leu Pro Lys Asp Glu Arg Pro His Phe
                305                 310                 315

Tyr Thr Leu Tyr Leu Glu Glu Pro Asp Ser Ser Gly His Ser Tyr
                320                 325                 330

Gly Pro Val Ser Ser Glu Val Ile Lys Ala Leu Gln Arg Val Asp
                335                 340                 345

Gly Met Val Gly Met Leu Met Asp Gly Leu Lys Glu Leu Asn Leu
                350                 355                 360

His Arg Cys Leu Asn Leu Ile Leu Ile Ser Asp His Gly Met Glu
                365                 370                 375

Gln Gly Ser Cys Lys Lys Tyr Ile Tyr Leu Asn Lys Tyr Leu Gly
                380                 385                 390

Asp Val Lys Asn Ile Lys Val Ile Tyr Gly Pro Ala Ala Arg Leu
                395                 400                 405

Arg Pro Ser Asp Val Pro Asp Lys Tyr Tyr Ser Phe Asn Tyr Glu
                410                 415                 420

Gly Ile Ala Arg Asn Leu Ser Cys Arg Glu Pro Asn Gln His Phe
                425                 430                 435
```

-continued

```
Lys Pro Tyr Leu Lys His Phe Leu Pro Lys Arg Leu His Phe Ala
                440                 445                 450

Lys Ser Asp Arg Ile Glu Pro Leu Thr Phe Tyr Leu Asp Pro Gln
                455                 460                 465

Trp Gln Leu Ala Leu Asn Pro Ser Glu Arg Lys Tyr Cys Gly Ser
                470                 475                 480

Gly Phe His Gly Ser Asp Asn Val Phe Ser Asn Met Gln Ala Leu
                485                 490                 495

Phe Val Gly Tyr Gly Pro Gly Phe Lys His Gly Ile Glu Ala Asp
                500                 505                 510

Thr Phe Glu Asn Ile Glu Val Tyr Asn Leu Met Cys Asp Leu Leu
                515                 520                 525

Asn Leu Thr Pro Ala Pro Asn Asn Gly Thr His Gly Ser Leu Asn
                530                 535                 540

His Leu Leu Lys Asn Pro Val Tyr Thr Pro Lys His Pro Lys Glu
                545                 550                 555

Val His Pro Leu Val Gln Cys Pro Phe Thr Arg Asn Pro Arg Asp
                560                 565                 570

Asn Leu Gly Cys Ser Cys Asn Pro Ser Ile Leu Pro Ile Glu Asp
                575                 580                 585

Phe Gln Thr Gln Phe Asn Leu Thr Val Ala Glu Glu Lys Ile Ile
                590                 595                 600

Lys His Glu Thr Leu Pro Tyr Gly Arg Pro Arg Val Leu Gln Lys
                605                 610                 615

Glu Asn Thr Ile Cys Leu Leu Ser Gln His Gln Phe Met Ser Gly
                620                 625                 630

Tyr Ser Gln Asp Ile Leu Met Pro Leu Trp Thr Ser Tyr Thr Val
                635                 640                 645

Asp Arg Asn Asp Ser Phe Ser Thr Glu Asp Phe Ser Asn Cys Leu
                650                 655                 660

Tyr Gln Asp Phe Arg Ile Pro Leu Ser Pro Val His Lys Cys Ser
                665                 670                 675

Phe Tyr Lys Asn Asn Thr Lys Val Ser Tyr Gly Phe Leu Ser Pro
                680                 685                 690

Pro Gln Leu Asn Lys Asn Ser Ser Gly Ile Tyr Ser Glu Ala Leu
                695                 700                 705

Leu Thr Thr Asn Ile Val Pro Met Tyr Gln Ser Phe Gln Val Ile
                710                 715                 720

Trp Arg Tyr Phe His Asp Thr Leu Leu Arg Lys Tyr Ala Glu Glu
                725                 730                 735

Arg Asn Gly Val Asn Val Val Ser Gly Pro Val Phe Asp Phe Asp
                740                 745                 750

Tyr Asp Gly Arg Cys Asp Ser Leu Glu Asn Leu Arg Gln Lys Arg
                755                 760                 765

Arg Val Ile Arg Asn Gln Glu Ile Leu Ile Pro Thr His Phe Phe
                770                 775                 780

Ile Val Leu Thr Ser Cys Lys Asp Thr Ser Gln Thr Pro Leu His
                785                 790                 795

Cys Glu Asn Leu Asp Thr Leu Ala Phe Ile Leu Pro His Arg Thr
                800                 805                 810

Asp Asn Ser Glu Ser Cys Val His Gly Lys His Asp Ser Ser Trp
                815                 820                 825

Val Glu Glu Leu Leu Met Leu His Arg Ala Arg Ile Thr Asp Val
```

-continued

```
                        830                   835                   840
Glu His Ile Thr Gly Leu Ser Phe Tyr Gln Gln Arg Lys Glu Pro
                    845                   850                   855
Val Ser Asp Ile Leu Lys Leu Lys Thr His Leu Pro Thr Phe Ser
                860                   865                   870
Gln Glu Asp
```